United States Patent [19]

Phillips

[11] Patent Number: 5,151,578
[45] Date of Patent: Sep. 29, 1992

[54] ANISOTROPICALLY BENDABLE HEATING PAD

[76] Inventor: Jerry G. Phillips, 6800 Cypress Rd. #304, Plantation, Fla. 33317

[21] Appl. No.: 751,555

[22] Filed: Aug. 29, 1991

[51] Int. Cl.⁵ .......................... H05B 3/34; A61F 7/00
[52] U.S. Cl. .................... 219/549; 219/212; 219/527; 219/528; 128/399
[58] Field of Search ............... 219/211, 212, 526, 527, 219/528, 529, 535, 546, 548, 549, 202, 550; 338/210, 211, 212, 213; 392/443; 128/399, 400, 401, 402, 403; 165/46

[56]  References Cited

U.S. PATENT DOCUMENTS

| | | | |
|---|---|---|---|
| 2,797,296 | 6/1957 | Fowler et al. | |
| 2,953,671 | 9/1960 | Allen | 219/46 |
| 3,281,578 | 10/1966 | Chapman | 219/528 |
| 3,539,767 | 11/1970 | Eisler | 219/213 |
| 3,906,185 | 9/1975 | Gross et al. | 219/523 |
| 4,021,640 | 5/1977 | Gross et al. | 219/211 |
| 4,736,088 | 4/1988 | Bart | 219/211 |

Primary Examiner—Bruce A. Reynolds
Assistant Examiner—Michael D. Switzer
Attorney, Agent, or Firm—Alvin S. Blum

[57] ABSTRACT

An electric heating pad is provided with an anisotropic stiffening member that provides considerable rigidity in a first direction and considerable flexibility in a second direction transverse to the first direction. The stiffening member is provided with many elongate parallel corrugations, ridges or channels to provide unidirectional stiffness in the direction of the long axis of the channels. When the heating pad is used in a vertical position with the channels running vertically, the pad is prevented from collapsing or folding over on itself by the stiffening member while it is flexible in the horizontal direction to conform to a body part. This feature is especially useful for heating an aching back while sitting upright. The pad is also useful for wrapping around a limb and is provided with a strap for that purpose.

18 Claims, 2 Drawing Sheets

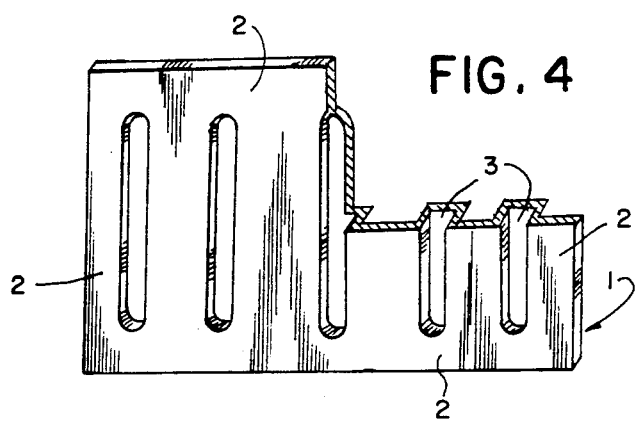
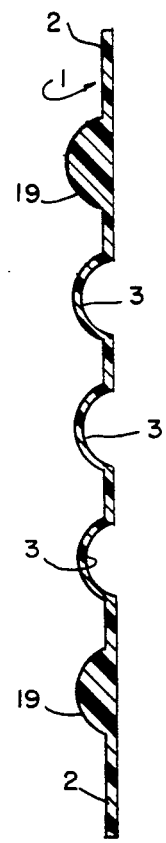
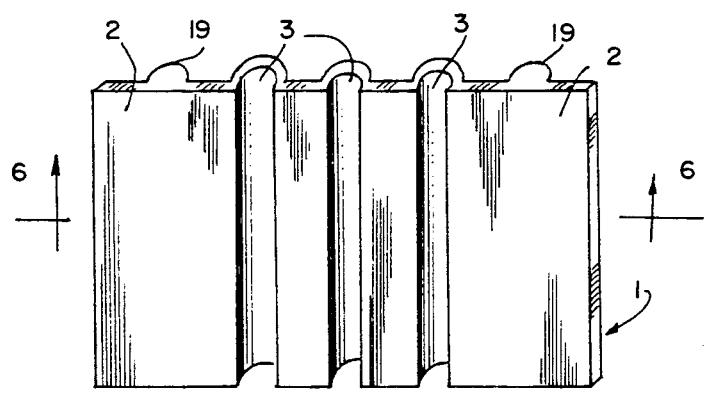
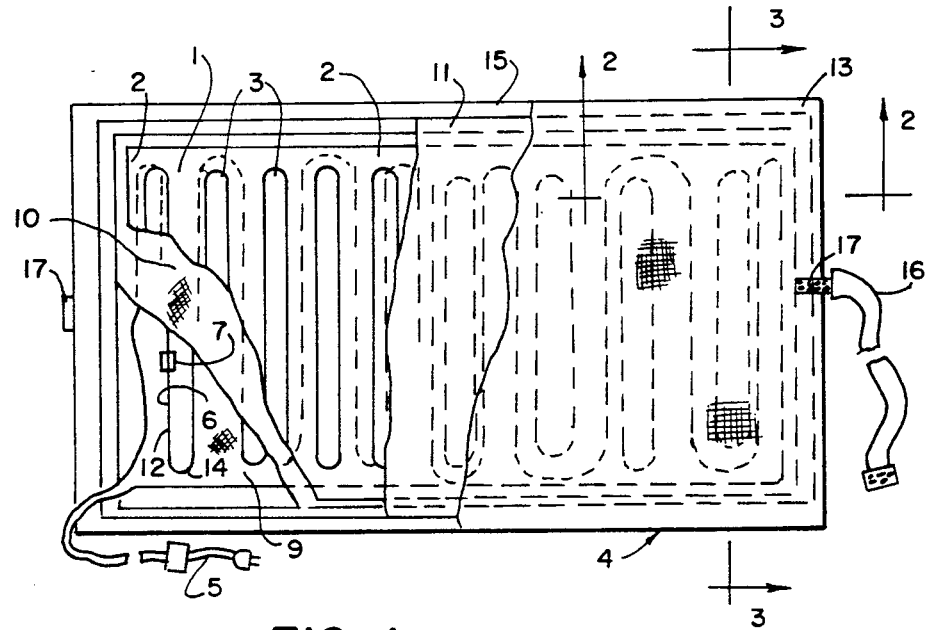

ANISOTROPICALLY BENDABLE HEATING PAD

BACKGROUND OF THE INVENTION

This invention relates to electrical devices for applying heat to the body of a person, and more particularly to electric heating pads constructed so as to remain flat when applied to a vertical body surface.

Electric heating pads are available in a variety of special configurations for special purposes, such as U.S. Pat. No. 3,953,671 for warming a cow's udder. The general public favors a simple planar, rectangular shape having a comfortable fabric outer surface, and sufficient flexibility for conforming to most body surfaces to which they are applied. These generally have their electrical resistance heating wire elements sealed within a water-tight rubber envelope, and have a large surface area that makes them versatile enough for most purposes. The pads in general use are sold with a warning to the user to avoid lying on the pad. When used in hospitals, nursing rules require that the patient must be sitting up or in prone position if this type of heating is applied to the back, and outpatients are instructed to follow these rules also. Back problems that can be temporarily relieved by application of heat are very common. Consequently, a most common use for electric heating pads is to the back while the user is sitting upright in a chair or bed. With the pad vertical between back and chair, any movement of the user may allow the pad to collapse or fold upon itself. When next the back is rested upon the crumpled pad, it is subjected to stresses that tend to break the wires, the user is subjected to concentrated heat below the useful area, and an uncomfortable bulge appears where once there was a smooth, flat, uniformly warm area.

SUMMARY OF THE INVENTION

It is, accordingly, an object of the invention to provide a heating pad that will be more stable when held vertically, resisting collapsing to provide a more uniform and comfortable heat source when applied to the back of a sitting user. It is another object of the invention to provide a heating pad that will be less subject to damage when used under certain common circumstances. It is yet another object of the invention that it can be applied more easily to curving surfaces.

The heating pad of the invention includes sealed, electrically resistive elements that convert into heat electrical energy applied thereto. The pad of the invention is substantially planar in shape. A stiffening member is incorporated into the pad. This stiffening member is a thin sheet of flexible material with parallel ridges all running in a first direction. These ridges inhibit bending in said first direction and permit bending in a second direction transverse to the first direction. When the pad is used in a vertical position with the ridges aligned in a vertical direction, the stiffening ridges prevent the pad from collapsing while it may still be bent around the body in the transverse direction. Consequently it is better able to conform to a body part for closer and more effective heating contact with the body than a rigid plate would provide. The pad may be rolled up for transport and storage. It may be rolled around a limb and held in place by a simple fastening arrangement.

These and other objects, advantages and features of the invention will become more apparent when the detailed description is considered in conjunction with the drawings.

BRIEF DESCRIPTION OF THE DRAWINGS

FIG. 1 is a top view of the invention with various layers partially broken away.

FIG. 4 is a perspective view of a stiffening member of the invention partially broken away with thickness exaggerated.

FIG. 5 is a perspective view of another embodiment of a stiffening member of the invention.

FIG. 6 is a sectional view taken along line 6—6 of FIG. 5.

DETAILED DESCRIPTION OF PREFERRED EMBODIMENTS

Referring now first to FIGS. 5 and 6, a stiffening member 1 of the invention is comprised of a thin sheet plastic material that may be extruded or molded. It has two flat lateral margins 2 and a series of parallel, elongate channels 3 and thickened ridges 19. It may be made of a thin, fireproof plastic. It is shown with thickness exaggerated for illustrative purposes. The parallel, longitudinal channels and ridges provide greatly increased rigidity in a direction parallel to their long axes, while the member remains quite flexible in the transverse direction. The ridges or channels may have various shapes and sizes and may be provided in various combinations. It may be manufactured inexpensively by extrusion. The member may be joined to other layers of the heating pad by stitching, heat sealing, adhesives and the like, as desired.

The stiffening member shown in FIG. 5 is preferably formed by molding, stamping or thermoforming. The flat margins 2 extend around all edges. The channels 3 do not extend to the margins. Both designs for a stiffening member are arranged to provide anistropic properties, stiff in one direction, flexible in a transverse direction. The channels may have various shapes and sizes.

Figure 2:
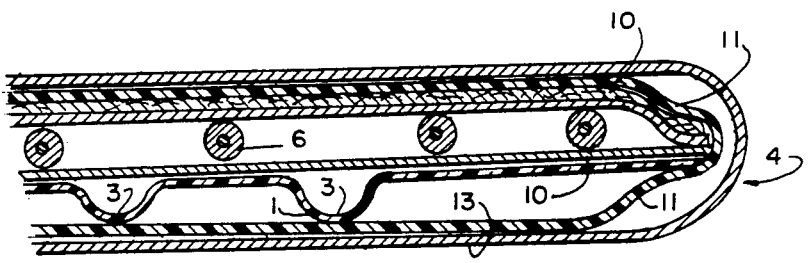
FIG. 2 is a sectional view taken along line 2—2 of FIG. 1.
Figure 3:
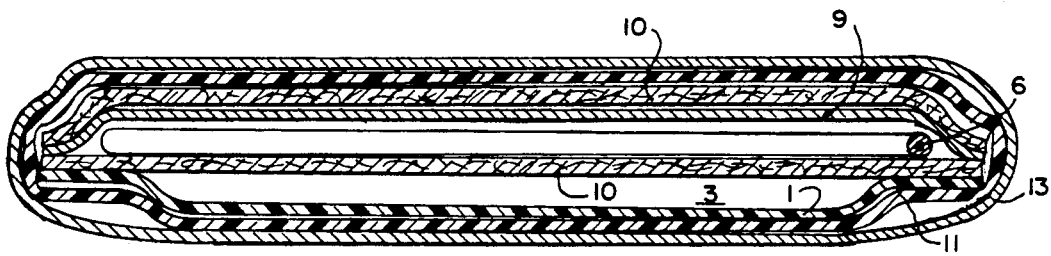
FIG. 3 is a sectional view taken along line 3—3 of FIG. 1.

Referring now to FIGS. 1-3, a heating pad 4 of the invention is shown with an electric power cord 5 electrically connected to a sinuously looped, or meander pattern of electrically resistive heating wire 6 with a thermal switch 7. This is conventional construction. Only a single resistance wire circuit 6 is shown, whereas there will generally be a plurality of circuits and arrangements for switching for selecting different heat levels. For clarity of illustration, these are omitted from the drawing.

The wires 6 are sewn to a supporting fabric 9. The wires on the supporting fabric are sandwiched between two soft cloth layers 10 to cushion the wires. The sandwiched wires are then enclosed in a water-tight envelope 11. The water tight envelope is then enclosed in a removable and washable soft fabric envelope 13 for comfortable body contact. This is all conventional construction and results in a heating pad that is always in danger of folding on itself and instructions specifically warn against using if it has sharp folds. These may cause wire breakage or hot spots much hotter than expected.

The unique aspect of the invention is the stiffening member 1. It is shown on one side of the heating pad, between the cushioning cloth layer 10 and one broad face of the water-tight envelope 11. The channels extend in a direction parallel to the long loop segments 12 of the heating wires and the flat margins 2 of the stiffening member 1 extend over the transverse connections 14 of wire between the long loops. The heating pad 4 will easily bend in the direction transverse to the long axis of the channels 3, but the channels cause the stiffening member to resist bending in a direction parallel to the long axis of the channels. Consequently, the heating pad 4 is very resistant to folding over and collapsing when used in the vertical position with upper margin 15 upright. And the ease with which it will bend in the horizontal direction makes it readily conform to a body part, such as the back.

This structure is also very useful for encircling a limb, wherein it may be held in place by a strap 16 with hook and loop fastener elements 17.

Figure 7:
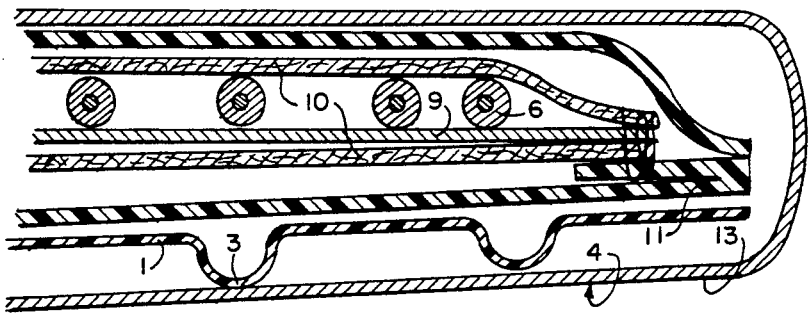
FIG. 7 is a sectional view of another embodiment of the invention.
Figure 8:
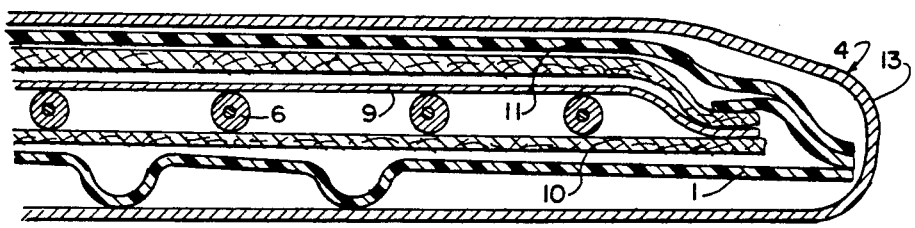
FIG. 8 is a sectional view of another embodiment of the invention.

The stiffening element may be optionally located at other positions in the pad, such as outside the water tight envelope 11 as shown in FIG. 7, or forming one face of the water tight envelope as in FIG. 8.

The electrical resistance heating element may be a film type of heating element well known in the art as exemplified by U.S. Pat. No. 3,539,767 issued Nov. 10, 1970 to Eisler.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

I claim:

1. A planar heating pad that is substantially rigid in a first direction and substantially flexible in a second direction transverse to the first direction, said heating pad comprising:
    a) at least one electrically resistive heating means arranged for heating substantially uniformly a large surface area;
    b) electrical connection means for connecting a source of electric power to said heating means;
    c) web means for supporting and protecting said heating means, said web means enclosing said heating means, said web means having two broad faces extending substantially in closely spaced parallel planes;
    d) a water-tight envelope means for protecting said heating means from exposure to moisture, said envelope means closely enclosing said web means;
    e) a flexurally anisotropic stiffening member means for making said heating pad rigid in a first direction and flexible in a second direction transverse to said first direction, both said directions being in a plane parallel to said broad faces of said web means, said stiffening member means being substantially planar and arranged in parallel relationship to said broad faces and extending over said large surface area; and
    f) a removable outer covering arranged to enclose said water-tight envelope means and said stiffening member means therein to thereby provide a broad area heating pad having a thickness that is small relative to said area and that bends readily in a second direction for conforming to body contours and that resists bending in a first direction transverse to said second direction, where both directions are in a common plane parallel to said broad faces.

2. The heating pad according to claim 1, in which said stiffening member means is a thin web having a plurality of elongate channels therein that are substantially parallel to one another, said channels having long axes that extend in said first direction to inhibit bending in said first direction and short axes that extend in said second direction to enhance bending in said second direction.

3. The heating pad according to claim 2, in which said stiffening member means is disposed between said web means and said water-tight envelope means.

4. The heating pad according to claim 2, in which said stiffening member means is disposed between said water-tight envelope means and said outer covering.

5. The heating pad according to claim 2, in which said stiffening member means comprises one broad face of said water-tight envelope means.

6. The heating pad according to claim 2, in which said electrically resistive heating means is film.

7. The heating pad according to claim 2, in which said electrically resistive heating means is wire.

8. The heating pad according to claim 7, in which said wire is arranged in long loops and the long axes of said loops are parallel to said first direction.

9. The heating pad according to claim 2, in which said outer covering is provided with fastening means on two opposed edges thereof for removably approximating said edges for more closely engaging a body part therewith.

10. The heating pad according to claim 1, in which said stiffening member means is a thin web having a plurality of elongate stiffening elements therein, said stiffening elements selected from the group of stiffening elements consisting of channels, and thickened ridges, said stiffening elements being substantially parallel to one another and having long axes that extend in said first direction and short axes that extend in said second direction to enhance stiffness more in said first direction than in said second direction.

11. The heating pad according to claim 10, in which said stiffening member means is arranged between said web means and said water-tight envelope means.

12. The heating pad according to claim 10, in which said stiffening member means is arranged between said water-tight envelope means and said outer covering.

13. The heating pad according to claim 10, in which said stiffening member means comprises one broad face of said water-tight envelope means.

14. The heating pad according to claim 10, in which said heating means is wire.

15. The heating pad according to claim 10, in which said heating means is film.

16. A thin, flat electric heating pad that is flexurally anisotropic to resist bending in a first, vertical direction and to permit bending in a second, horizontal direction when applied to the upright back of a seated user, said heating pad comprising:

a) at least one electrically resistive heating means arranged for heating substantially uniformly a large surface area;

b) electrical connection means for connecting a source of electric power to said heating means;

c) web means for supporting and protecting said heating means, said web means enclosing said heating means, said web means having two broad faces extending substantially in closely spaced parallel planes.

d) a water-tight envelope means for protecting said heating means from exposure to moisture, said envelope means enclosing said web means;

e) a flexurally anisotropic stiffening member means for making said heating pad rigid in a first, vertical direction and to permit bending freely in a second, horizontal direction for enhanced conformation to the back of a user when seated upright, said stiffening member means being substantially planar and arranged in parallel relationship to said broad faces and extending over said large surface area; and f) a removable outer covering arranged to enclose said water-tight envelope means and said stiffening member means therein to thereby provide a broad area heating pad having a thickness that is small relative to said area and that bends readily in a second direction for conforming to body contours and that resists bending in a first direction transverse to said second direction.

17. The heating pad according to claim 16 in which said stiffening member means is a thin web arranged in a plane and having a plurality of long narrow stiffening elements connected thereto and extending from said plane, said stiffening elements selected from the group of elements consisting of channels and thickened ridges, said stiffening elements having long axes that all extend in said first direction and short axes that all extend in said second direction to thereby provide greater stiffness in said first direction than in said second direction.

18. The heating pad according to claim 17, in which those portions of said stiffening elements which extend from said plane are unattached to one another to permit free bending in said second direction.

* * * * *